US00PP22683P2

(12) United States Plant Patent
Bergman

(10) Patent No.: US PP22,683 P2
(45) Date of Patent: Apr. 24, 2012

(54) ***CHRYSANTHEMUM* PLANT NAMED 'CIDZ0013'**

(50) Latin Name: *Chrysanthemum×morifolium*
Varietal Denomination: CIDZ0013

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/136,061

(22) Filed: Jul. 21, 2011

(51) Int. Cl.
*A01H 5/00* (2006.01)

(52) U.S. Cl. ..... Plt./286

(58) Field of Classification Search ..... Plt./286, Plt./297
See application file for complete search history.

*Primary Examiner* — Howard Locker
(74) *Attorney, Agent, or Firm* — Joshua L. Price

(57) ABSTRACT

A new *Chrysanthemum* plant named 'CIDZ0013' particularly distinguished by the single-daisy form inflorescences, spoon-shaped ray florets, intense light purple ray floret color with a slow-developing green disc, medium green foliage, with a compact and full plant habit.

1 Drawing Sheet

Latin name of the genus and species of the plant claimed: *Chrysanthemum×morifolium.*

Varietal denomination: 'CIDZ0013'.

BACKGROUND OF THE NEW PLANT

The present invention comprises a new *Chrysanthemum*, botanically known as *Chrysanthemum×morifolium*, and hereinafter referred to by the variety name 'CIDZ0013'.

'CIDZ0013' is a product of a planned breeding program. The new cultivar has single-daisy form inflorescences, spoon-shaped ray florets, intense light purple ray floret color with a slow-developing green disc, medium green foliage, with a compact and full plant habit.

'CIDZ0013' originated from a hybridization made in June 2007 in a controlled breeding environment in Salinas, Calif., USA. The female parent was the proprietary plant designated 'YB-A3545', unpatented, with purple ray floret color, fewer inflorescences, and a one week slower flowering response.

The male parent of 'CIDZ0013' was an unpatented, proprietary plant identified as 'YB-A6845' with bronze ray floret color and produces pollen. The resultant seed was sown in October 2007 in Fort Myers, Fla., USA.

'CIDZ0013' was selected as one flowering plant within the progeny of the stated cross in March 2008 in a controlled environment in Fort Myers, Fla., USA.

The first act of asexual reproduction of 'CIDZ0013' was accomplished when vegetative cuttings were propagated from the initial selection in June 2008 in a controlled environment in Fort Myers, Fla., USA.

BRIEF SUMMARY OF INVENTION

Horticultural examination of plants grown from cuttings of the plant initiated in June 2008, and continuing thereafter, has demonstrated that the combination of characteristics as herein disclosed for 'CIDZ0013' are firmly fixed and are retained through successive generations of asexual reproduction.

'CIDZ0013' has not been observed under all possible environmental conditions. The phenotype may vary significantly with variations in environment such as temperature, light intensity and day length.

A Plant Breeder's Right for this cultivar was applied for in Canada on Aug. 17, 2010 (10-7071). 'CIDZ0013' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIDZ0013' with colors being as true as possible with an illustration of this type.

The photographic drawing shows four flowering potted plants of the new variety and a close-up of the inflorescences.

DETAILED BOTANICAL DESCRIPTION

The plant descriptions, measurements and aforementioned photographs were taken in Gilroy, Calif. in early May 2011 under natural light. These plants were propagated and grown in Nipomo, Calif. and shipped to Gilroy, Calif. for the data collection and photographs. These plants were approximately 11 weeks of age; grown as four plants together in a six inch pot under greenhouse trial conditions Color references are made to The Royal Horticultural Society Colour Chart (R.H.S.) 2001.

TABLE 1

DIFFERENCES BETWEEN THE NEW VARIETY 'CIDZ0013' AND A MOST SIMILAR VARIETY

| | 'CIDZ0013' | 'Yolaporte' (U.S. Plant Pat. No. 13,917) |
|---|---|---|
| Flowering response: | Faster | Slower |
| Inflorescence quality: | Greater | Fewer |
| Plant habit: | Fuller/more dense habit | Less full/dense |

Plant:

*Form, growth and habit.*—Herbaceous pot-type, stems upright and outwardly spreading, freely branching, uniform and strong and growth habit.

*Plant height.*—27.0-28.0 cm.
*Plant height (inflorescence included).*—36.0-38.0 cm.
*Plant width.*—20.0 cm.

Roots:
*Number of days to initiate roots.*—About 4 days at about 22 degrees C.
*Number of days to produce a rooted cutting.*—About 10 days at 22 degrees C.
*Type.*—Fine, fibrous, free branching.
*Color.*—RHS N155B but whiter.

Foliage:
*Arrangement.*—Alternate, simple.
*Immature, leaf color, upper surface.*—RHS 139A but lighter.
*Lower surface.*—RHS 139A.
*Mature, leaf color, upper surface.*—RHS 139A but lighter.
*Lower surface.*—RHS 139A.
*Length.*—7.0-9.5 cm.
*Width.*—3.8-4.8 cm.
*Shape.*—Ovate.
*Base shape.*—Attenuate.
*Apex shape.*—Mucronulate.
*Margin.*—Palmately lobed; irregularly serrate.
*Texture, upper surface.*—Bifid T-shaped hairs.
*Lower surface.*—Bifid T-shaped hairs.
*Color of veins, upper surface.*—RHS 144B.
*Color of veins, lower surface.*—RHS 144B.
*Petiole color.*—RHS 144B.
*Length.*—2.4-2.8 cm.
*Diameter.*—0.2-0.25 cm.
*Texture.*—Bifid T-shaped hairs.

Stem:
*Quantity of main branches per plant.*—5-7.
*Color of stem.*—RHS 137B but appears lighter due to hairs.
*Length of stem.*—18.0-21.0 cm.
*Diameter.*—0.5 cm.
*Length of internodes.*—1.0-3.0 cm.
*Texture.*—Bifid T-shaped hairs.
*Color of peduncle.*—RHS 137B but appears lighter due to hairs.
*Length of peduncle.*—8.0-8.5 cm.
*Peduncle diameter.*—0.2 cm.
*Texture.*—Bifid T-shaped hairs.

Inflorescence:
*Type.*—Compositae type, solitary, single daisy-type inflorescences with spoon-shaped ray florets, borne terminally above foliage, ray florets arranged acropetally on a capitulum.
*Quantity of short days to flowering (response time).*—About 8 weeks.
*Quantity of inflorescences per plant.*—27-35.
*Lastingness of individual blooms on the plant.*—About 4 weeks.
*Fragrance.*—Slightly spicy.

Bud (just when opening/showing color):
*Color.*—RHS 71A but darker.
*Length.*—1.3-1.4 cm.
*Width.*—1.0-1.1 cm.
*Shape.*—Oblate.

Immature inflorescence:
*Diameter.*—5.5-6.0 cm.
*Color of ray florets, upper surface.*—RHS N79C but barely visible because petals are closed over.
*Lower surface.*—RHS 70A.

Mature inflorescence:
*Diameter.*—8.5-9.0 cm.
*Depth.*—3.5 cm.
*Total diameter of disc.*—2.0-2.2 cm.
*Receptacle height.*—0.6-0.7 cm.
Receptacle diameter.—0.8-0.9 cm.

Ray florets:
*Average quantity of florets.*—18-23 in 1 whorl.
*Color of florets, upper surface.*—RHS N79C.
*Lower surface.*—Closest to RHS 72B.
*Length.*—2.8-4.3 cm.
*Width.*—0.35-0.45 cm.
*Shape.*—Spoon.
*Apex shape.*—Praemorse.
*Margin.*—Entire (fused).
*Texture, upper surface.*—Papillose.
*Lower surface.*—Papillose.

Disc florets:
*Average quantity of florets.*—Approximately 130.
*Color of florets.*—RHS 155C but more green with RHS 3B apex: discs before opening appear to have a more green apex of about RHS 144B.
*Length.*—0.5 cm.
*Width.*—0.1 cm.
*Shape.*—Tubular, elongated.
*Apex shape.*—Acute, 5 pointed.

Phyllaries:
*Quantity.*—20-25.
*Color, upper surface.*—RHS 137B.
*Lower surface.*—Between RHS 137A and RHS 137B but appears lighter due to hairs.
*Length.*—0.6-0.7 cm.
*Width.*—0.2-0.25 cm.
*Shape.*—Lanceolate.
*Apex shape.*—Acute.
*Base.*—Fused.
*Margins.*—Entire; papery.
*Texture, upper surface.*—Glabrous.
*Lower surface.*—Bifid T-shaped hairs.

Reproductive organs:
*Pistil.*—1.
*Found on both florets.*—Yes.
*Length.*—0.6 cm.
*Style color.*—RHS 1C but more green.
*Style length.*—0.5 cm.
*Stigma color.*—RHS 14B.
*Stigma shape.*—Bi-parted.
*Ovary color.*—Not observed; ovary too immature to observe any color due to maturing with pollination.
*Stamens.*—4.
*Found on only disc florets.*—Yes.
*Color of filaments.*—About RHS 2D.
*Length filaments.*—0.2-0.3 cm.
*Anther color.*—RHS 21C.
*Anther length.*—0.1 cm.
*Anther shape.*—Oblong.
*Color of pollen.*—Not observed.
*Pollen amount.*—Not observed.
*Fertility/seed set.*—Has not been observed on this hybrid.

Disease/pest resistance: Disease/pest resistance has not been observed on this hybrid.

What is claimed:

1. A new and distinct variety of *Chrysanthemum* plant named 'CIDZ0013' substantially as illustrated and described herein.

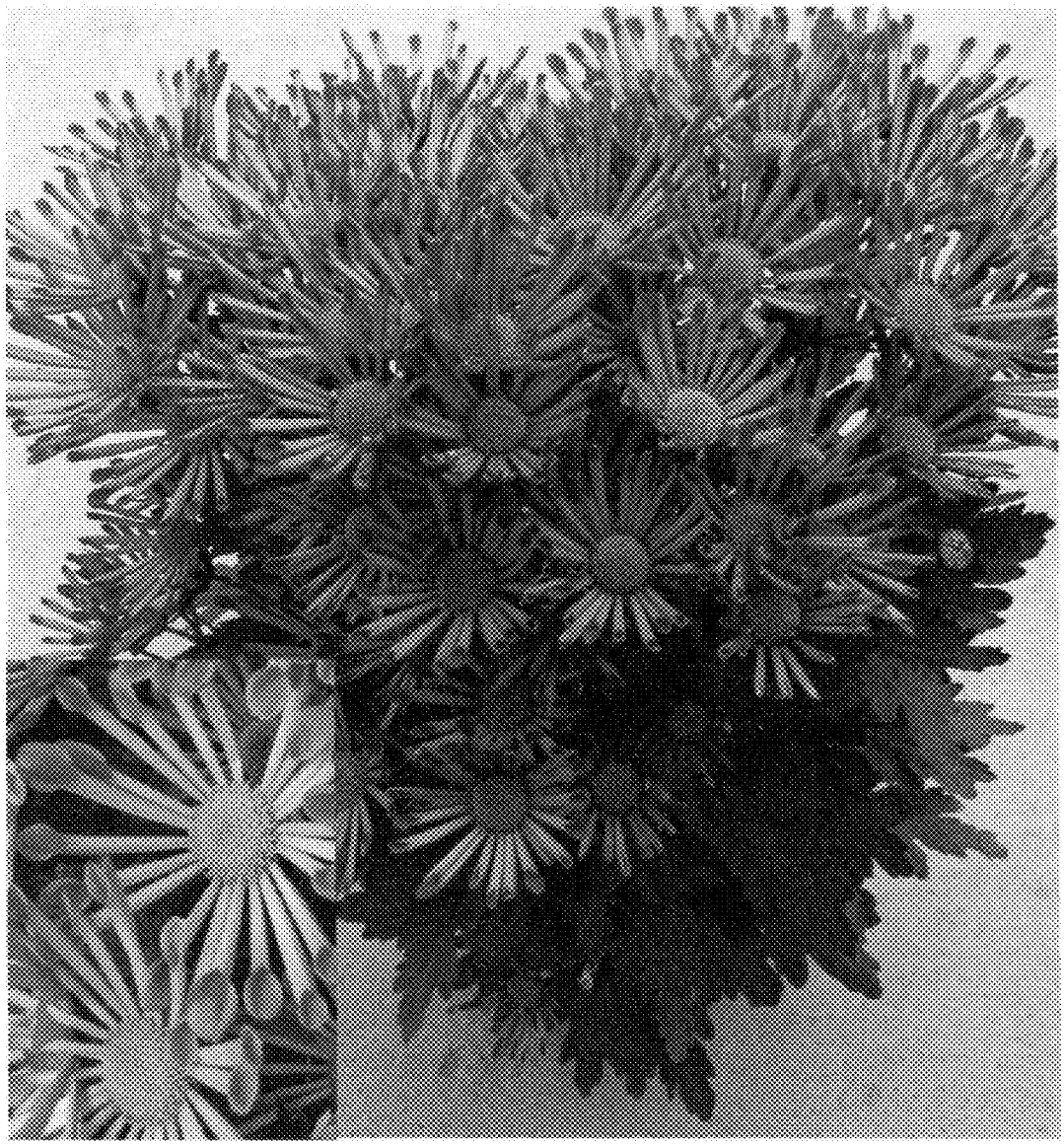

* * * * *